(12) United States Patent
Moye-Sherman et al.

(10) Patent No.: US 7,390,834 B2
(45) Date of Patent: Jun. 24, 2008

(54) CYANOPHENOXY CARBOXYLIC ACID COMPOUNDS AND COMPOSITIONS FOR DELIVERING ACTIVE AGENTS

(75) Inventors: Destardi Moye-Sherman, Newburgh, NY (US); David Gschneidner, Thornwood, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 70 days.

(21) Appl. No.: 11/462,631

(22) Filed: Aug. 4, 2006

(65) Prior Publication Data

US 2006/0264356 A1 Nov. 23, 2006

Related U.S. Application Data

(63) Continuation of application No. 10/363,722, filed as application No. PCT/US01/41984 on Sep. 5, 2001, now Pat. No. 7,115,663.

(60) Provisional application No. 60/237,235, filed on Oct. 2, 2000, provisional application No. 60/230,331, filed on Sep. 6, 2000.

(51) Int. Cl.
*A61K 31/19* (2006.01)

(52) U.S. Cl. ........................ 514/559; 514/571

(58) Field of Classification Search ........................ None
See application file for complete search history.

(56) References Cited

U.S. PATENT DOCUMENTS 4,060,619 A * 11/1977 Philipp et al. ................ 514/291

5,574,016 A * 11/1996 Takasugi et al. .............. 514/18
6,289,286 B1 9/2001 Andersson et al.

FOREIGN PATENT DOCUMENTS

| WO | WO-99/63333 | 12/1999 |
| WO | WO-01/32130 A1 | 5/2001 |

OTHER PUBLICATIONS

Schultz et al, Journal of the American Chemical Society, Heteroatom Directed Photoarylation. Synthetic Potential of the Heteroatom Oxygen, 1978, 100(7), pp. 2150-2162.*
Kim et al, Canadian Journal of Microbiology, Bioengineering of poly(b-hydroxyalkanoates) for Advanced Materials Applications: Incorporation of Cyano and Nitrophenoxy Side Chain Substituents, 1995, 41(Suppl. 1), pp. 32-43.*
Hatano et al., "Synthesis of 2,4-Dicyanophenoxyacetic Acid and its Analogues." Agricultural and Biological Chemistry. Dec. 1973, vol. 12, p. 2919.
Leone-Bay, A. et al., "n-Acylated Alpha-Amino Acids as Novel Oral Delivery Agents for Proteins," Journal of Medicinal Chemistry, American Chemical Society, vol. 38, No. 21, Oct. 1995, pp. 4263-4269.
Milstein, S J, et al., "Partially Unfolded Proteins Efficiently Penetrate Cell Membranes—Implications for Oral Drug Delivery," Journal of Controlled Release, vol. 53, No. 1-3, Apr. 30, 1998, pp. 259-267.
Kim, D.Y., et al., "Evaluation of Various Carbon Substrates for the Biosynthesis of Polyhydroxyalkanoates Bearing Functional Groups by Pseudomonas Putida," International Journal of Biological Macromolecules, Oct. 2000, pp. 23-29.
Chinese Office Action in counterpart Chinese application.

* cited by examiner

*Primary Examiner*—Paul A. Zucker
(74) *Attorney, Agent, or Firm*—Darby & Darby

(57) ABSTRACT

Cyanophenoxy carboxylic acid compounds and compositions for the delivery of active agents are provided. Methods of administration, treatment of disease and preparation are provided as well.

9 Claims, No Drawings

CYANOPHENOXY CARBOXYLIC ACID COMPOUNDS AND COMPOSITIONS FOR DELIVERING ACTIVE AGENTS

This application is a continuation of U.S. Ser. No. 10/363,722, filed May 7, 2003, which is a national phase of PCT Application No. PCT/US01/41984, filed Sep. 5, 2001, which was published in English as International Publication No. WO 02/20466 and claims the benefit of U.S. Provisional Application Nos. 60/230,331 and 60/237,235, filed Sep. 6, 2000 and Oct. 2, 2000, respectively, all of which are herein incorporated by reference.

FIELD OF THE INVENTION

The present invention relates to cyanophenoxy carboxylic acid compounds for delivering active agents, such as biologically or chemically active agents, to a target. These compounds are well suited for forming non-covalent mixtures with active agents for oral, intracolonic, pulmonary, and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e., active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the following formula:

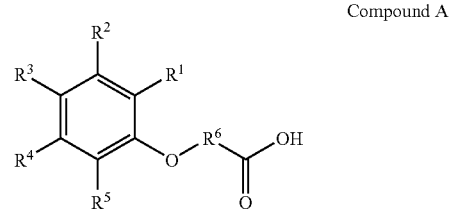

Compound A and salts thereof wherein $R^1$, $R^2$, $R^3$, $R^4$ and $R^5$ are independently H, —CN, —OH, —OCH$_3$, or halogen, at least one of $R^1$, $R^2$, $R^3$, $R^4$ and $R^5$ being —CN; and $R^6$ is $C_1$-$C_{12}$ linear or branched alkylene, alkenylene, arylene, alkyl(arylene) or aryl(alkylene), with the proviso that when $R^1$ is —CN, $R^4$ is H or —CN, and $R^2$, $R^3$, and $R^5$ are H, then $R^6$ is not methylene ((CH$_2$)$_1$).

In a preferred embodiment, $R^1$ is H or —CN. In another preferred embodiment, $R^4$ is H, —CN, or a halogen. In another preferred embodiment, the halogen is Cl.

Preferably, $R^6$ is $C_1$-$C_9$ alkylene. More preferably R is $C_8$-$C_9$ alkylene. According to a more preferred embodiment, $R^8$ is $C_4$-$C_7$ alkylene. According to another preferred embodiment, $R^6$ is (CH$_2$)$_1$, (CH$_2$)$_3$, (CH$_2$)$_4$, (CH$_2$)$_5$, (CH$_2$)$_7$, or (CH$_2$)$_9$.

In a preferred embodiment, $R^1$ is —CN. Preferably, $R^2$, $R^3$, $R^4$ and $R^5$ are H or halogen, preferably Cl. Preferably, $R^6$ is (CH$_2$)$_n$ where n is 1-12, preferably 2-9, more preferably 3-7, and more preferably 7 or $R^6$ is —(CH$_2$)-para-phenylene.

In another preferred embodiment, $R^3$ is —CN. Preferably, $R^1$, $R^2$, $R^4$ and $R^5$ are H or halogen, preferably Cl. Preferably, $R^6$ is (CH$_2$)$_n$ and n is 1-12, preferably 2-9, more preferably 3-7, and more preferably 7.

In another preferred embodiment, the compound comprises the compounds of Table 1 or salts thereof or mixtures thereof:

TABLE 1

Delivery Agent Compounds

| Cpd # | $R^1$ | $R^2$ | $R^3$ | $R^4$ | $R^5$ | $R^6$ |
|---|---|---|---|---|---|---|
| 1 | CN | H | H | H | H | $(CH_2)_1$ |
| 2 | CN | H | H | H | H | $(CH_2)_3$ |
| 3 | CN | H | H | H | H | $(CH_2)_4$ |
| 4 | CN | H | H | H | H | $(CH_2)_5$ |
| 5 | CN | H | H | H | H | $(CH_2)_7$ |
| 6 | CN | H | H | H | H | $(CH_2)_9$ |
| 7 | CN | H | Cl | H | H | $(CH_2)_4$ |
| 8 | H | H | CN | H | H | $(CH_2)_7$ |
| 9 | CN | H | H | H | H | $(CH_2)_1$-para-phenyl- |

The chemical structures of compounds 1-9 are shown below:

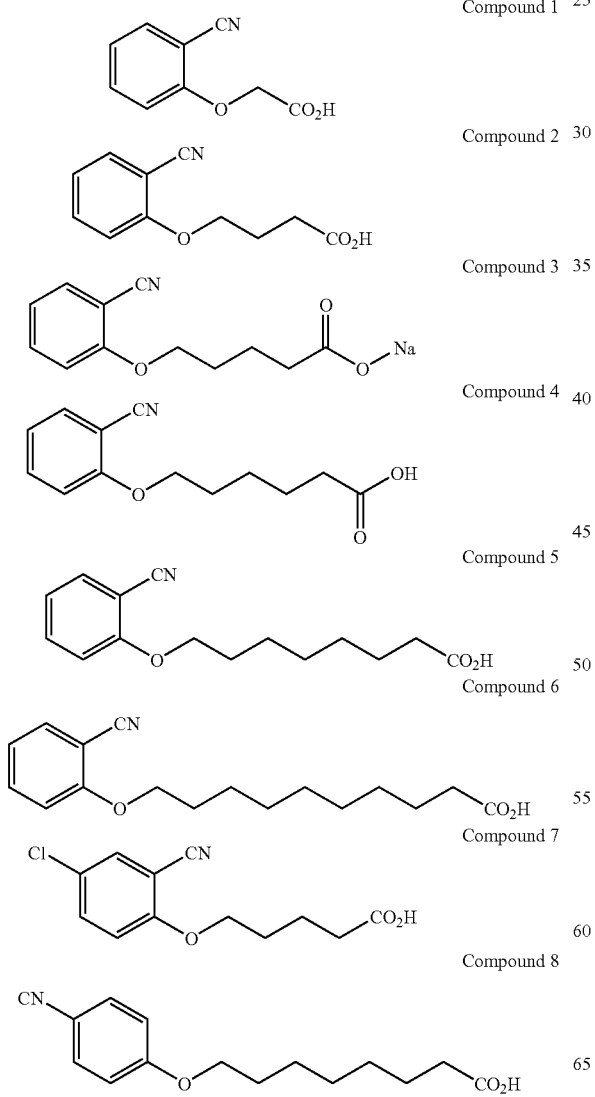

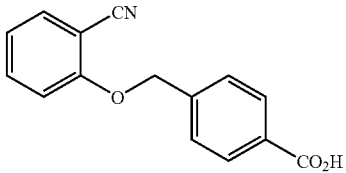

and salts thereof or mixture thereof.

The invention also provides a composition comprising at least one of the delivery agent compounds of the formulas above, and at least one active agent. These compositions deliver active agents to selected biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal in need of the active agent, by administering a composition comprising at one of the delivery agent compounds of the formulae above and the active agent to the animal. Preferred routes of administration include the oral, intracolonic and pulmonary routes.

Yet another embodiment is a method of treating a disease or for achieving a desired physiological effect in an animal in need thereof by administering an effective amount of the composition of the present invention.

Yet another embodiment is a method of preparing a composition of the present invention by mixing at least one delivery agent compound of the formulae above, and at least one active agent.

DETAILED DESCRIPTION OF THE INVENTION

Delivery Agent Compounds

The terms "alkyl" and "alkenyl" as used herein include linear and branched alkyl and alkenyl substituents, respectively.

The delivery agent compounds may be in the form of the carboxylic acid or salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

Salts of the delivery agent compounds of the present invention may be prepared by methods known in the art. For example, sodium salts may be prepared by dissolving the delivery agent compound in ethanol and adding aqueous sodium hydroxide.

In addition, poly amino acids and peptides comprising one or more of these delivery agent compounds may be used.

An amino acid is any carboxylic acid having at least one free amine group and includes naturally occurring and synthetic amino acids. Poly amino acids are either peptides (which are two or more amino acids joined by a peptide bond)

or are two or more amino acids linked by a bond formed by other groups which can be linked by, e.g., an ester or an anhydride linkage. Peptides can vary in length from dipeptides with two amino acids to polypeptides with several hundred amino acids. One or more of the amino acids or peptide units may be acylated or sulfonated.

The compounds described herein may be derived from amino acids and can be readily prepared from amino acids by methods within the skill of those in the art based upon the present disclosure and the methods described in International Patent Publication Nos. WO 96/30036 and WO 97/36480 and U.S. Pat. Nos. 5,643,957 and 5,650,386. For example, the delivery agent compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, N.Y. (1981), the disclosure of which is hereby incorporated herein by reference.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, methanol, tetrahydrofuran and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent compound may contain a polymer conjugated to it by a linkage group selected from the group consisting of —NHC(O)NH—, —C(O)NH—, —NHC(O), —OOC—, —COO—, —NHC(O)O—, —OC(O)NH—, —CH$_2$NH —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond. According to one preferred embodiment, the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastrointestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α, β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Delivery Systems

The composition of the present invention comprises one or more delivery agent compounds of the present invention (including their salts and polymeric derivatives), and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the delivery agent compound with the solid form of the active agent. Alternately, a solid may be obtained from a solution of the delivery agent compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to, birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the delivery agent compounds and compositions of the present invention are useful in orally administering active agents, especially those that are not ordinarily orally deliverable, or those for which improved delivery is desired.

The compositions comprising the delivery agent compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference (54$^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
| --- | --- |
| Growth hormones | Growth disorders |
| Interferons, including α, β and γ. | Viral infection, including chronic cancer and multiple sclerosis |
| Interleukin-1; interleukin-2. | Viral infection; cancer |
| Insulin; Insulin-like growth factor IGF-1. | Diabetes |
| Heparin | Thrombosis; prevention of blood coagulation |
| Calcitonin. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium; Vancomycin | Asthma; allergies |
| Desferrioxamine (DFO) | Iron overload |
| Parathyroid hormone (PTH), including its fragments. | Osteoporosis; Diseases of the bone |
| Antimicrobials | Infection including gram-positive bacterial infection |

-continued

| Active Agent | Disease and Physiological Effect |
|---|---|
| Vitamins | Vitamin deficiencies |
| Bisphosphonates | Osteoporosis; Paget's disease; Inhibits osteoclasts |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

Proton nuclear magnetic resonance ($^1$H NMR) analyses for the compounds listed below were conducted on a 300 MHz Bruker spectrometer using dimethyl sulfoxide (DMSO-$d_6$) as the solvent unless otherwise indicated.

EXAMPLE 1

Compound Preparation

1a: Preparation of Compound 1

A 3-neck 300 mL round-bottomed flask equipped with a reflux condenser, magnetic stir bar and a nitrogen inlet was charged with 5 g (1 equiv.) of 2-hydroxybenzonitrile, absolute ethanol 150 mL, and 15.7 mL (1 equivalent) of sodium ethoxide. This mixture was stirred at 25° C. for 15 minutes. Ethyl bromoacetate (4.6 mL, 1 equivalent) was then added dropwise over 10 minutes. The resulting mixture was heated to reflux (75° C.) for 72 hours.

The reaction mixture was cooled and the solids filtered off. The solvent was removed on a rotary evaporator. The crude residue was dissolved in methylene chloride (250 mL) and washed with saturated NaHCO$_3$ (3×100 mL), H$_2$O (1×100 mL) and brine (1×50 mL). The organic layer was dried to give the crude ester. The crude material was then dissolved in ethanol (150 mL) and water (10 mL). LiOH (4 g) was added and the resulting mixture was heated to reflux (75° C.) for 3 hours. The solution was cooled and the solvent removed. 100 mL of H$_2$O was added and the aqueous solution was acidified to a pH of about 2 with concentrated hydrochloric acid. The solution was cooled in a 4° C. refrigerator. A tan colored solid precipitated. This material was collected by vacuum filtration and dried on the high vacuum overnight to give 6.71 g of the product, 3-(2-cyanophenoxy) acetic acid (90% yield). Melting point: 179-181° C. Molecular Formula: C$_9$H$_7$NO$_3$. Combustion analysis: % C: 61.02 (calc'd), 60.69 (found); % H: 3.98(calc'd), 3.98 (found); % N: 7.91 (calc'd), 7.66 (found).

1b: Preparation of Compound 2

A 3-neck 300 mL round-bottomed flask equipped with a reflux condenser, magnetic stir bar and an N$_2$ inlet was charged with 5 g (1 equiv.) of 2-hydroxybenzonitrile, absolute ethanol 150 mL, and 15.7 mL (1 equivalent) of sodium ethoxide. This mixture was stirred at 25° C. for 15 minutes. Ethyl 4-bromobutyrate (6.0 mL, 1 equivalent) was then added dropwise over 10 minutes. The resulting mixture was heated to reflux (75° C.) for 72 hours.

The reaction mixture was cooled and the solids filtered off. The solvent was removed on a rotary evaporator. The crude residue was dissolved in methylene chloride (300 mL) and washed with saturated NaHCO$_3$ (2×100 mL), H$_2$O (1×100 mL) and brine (1×50 mL). The organic layer was dried to give the crude ester. The crude material was then dissolved in ethanol (150 mL) and water (10 mL). LiOH (5 grams) was added and the resulting mixture was heated to reflux (75° C.) for 3 hours. The solution was cooled and the solvent removed. 75 mL of H$_2$O was added and the aqueous solution was acidified to a pH of about 2 with concentrated HCl. The solution was cooled in a 4° C. refrigerator. A tan colored solid precipitated. This material was collected by vacuum filtration and dried on the high vacuum overnight to give the product, 4-(2-cyanophenoxy)butanoic acid (71% yield). Melting point: 127-128° C. Molecular Formula: C$_{11}$H$_{11}$NO$_3$. Combustion analysis: % C: 64.38 (calc'd), 64.01 (found); % H: 5.4(calc'd), 5.2(found); % N: 6.83 (calc'd), 6.74 (found).

1c: Preparation of Compound 3

A 3-neck 300 mL round-bottomed flask equipped with a reflux condenser, magnetic stir bar and a nitrogen inlet was charged with 4 g (1 equivalent) of 2-hydroxybenzonitrile, absolute ethanol 150 mL, and 12.5 mL (1 equivalent) of sodium ethoxide. This mixture was stirred at 25° C. for 15 minutes. Ethyl 5-bromovalerate (5.3 mL, 1 equivalent) was then added dropwise over 10 minutes. The resulting mixture was heated to reflux (80° C.) for 72 hours. The reaction mixture was cooled and the solids filtered off. The solvent was removed on a rotary evaporator. The crude residue was dissolved in methylene chloride (200 mL) and washed with saturated NaHCO$_3$ (2×100 mL), H$_2$O (1×50 mL) and brine (1×50 mL). The organic layer was dried to give the crude ester. The crude material was then dissolved in ethanol (150 mL) and water (10 mL) LiOH (3.5 g) was added and the resulting mixture was heated to reflux (80° C.) for 3 hours. The solution was cooled and the solvent removed. 75 mL of H$_2$O was added and the aqueous solution was acidified to a pH of approximately 2 with concentrated HCl. The flask was cooled by placing it in a 4° C. refrigerator for 4 hours. A tan colored solid precipitated. This material was collected by vacuum filtration and dried on the high vacuum overnight to give 6.2 g of material (84% yield). This material was further purified by recrystallization from ethyl acetate/hexanes (approximately 95/5) to give 5.3 g of 5-(2-cyanophenoxy) pentanoic acid. Melting point: 87-89° C. Combustion analysis: % C: 65.74 (calc'd), 65.52 (found); % H: 5.98 (calc'd), 5.86 (found); % N: 6.39 (calc'd), 6.38 (found). $^1$HNMR Analysis: (d$_6$-DMsO) δ 12.0, s, 1H (COOH); δ 7.73-7.62, m, 2H (aromatic CH's ortho and para to CN); δ 7.25, d, 1H, J=8.5 Hz (aromatic CH para to OR); δ 7.10, dt, 1H, J=0.7 and 6.8 Hz (aromatic CH ortho to OR); δ 4.16, t, 2H, J 7.5 Hz (CH$_2$ α to O); δ 2.33, t, 2H, J=7.2 Hz (CH$_2$ α to COOH); δ 1.80-1.64, m, 4H (remaining aliphatic CH$_2$'s).

1d: Preparation of Compound 4

A 3-neck 300 mL round-bottomed flask equipped with a reflux condenser, magnetic stir bar and an N$_2$ inlet was charged with 5 g (1 equivalent) of 2-hydroxybenzonitrile, absolute ethanol 150 mL, and 15.7 mL (1 equivalent) of sodium ethoxide. This mixture was stirred at 25° C. for 15 minutes. Ethyl 6-bromohexanoate (7.5 mL, 1 equiv.) was then added dropwise over 10 minutes. The resulting mixture was heated to reflux (75° C.) for 72 hours.

The reaction mixture was cooled and the solids filtered off. The solvent was removed on a rotary evaporator. The crude residue was dissolved in methylene chloride (300 mL) and washed with saturated $NaHCO_3$ (3×100 mL), $H_2O$ (1×100 mL) and brine (1×100 mL). The organic layer was dried to give the crude ester. The crude material was then dissolved in ethanol (150 mL) and water (15 mL). LiOH (7 g) was added and the resulting mixture was heated to reflux (75° C.) for 2 hours. The solution was cooled and the solvent removed. 125 mL of $H_2O$ was added and the aqueous solution was acidified to pH ~2 with concentrated HCl. The solution was cooled in a 4° C. refrigerator. A tan colored solid precipitated. This material was collected by vacuum filtration and dried on the high vacuum overnight to give the crude acid. This material was further purified by recrystallization from ethyl acetate/hexanes (95/5) to give 6.81 g of 6-(2-cyanophenoxy)hexanoic acid (70% yield). Melting point: 77-80° C. Karl Fisher: 1.26% $H_2O$. Molecular Formula with $H_2O$: C13H15SNO3*0.1652. Combustion analysis: % C: 66.09 (calc'd), 66.19 (found); % H: 6.54 (calc'd), 6.36 (found); % N: 5.93 (calc'd), 5.9 (found). $^1$H NMR Analysis: ($d_6$-DMSO): δ 12.0, s, 1H; 7.72-7.61, m, 2H; 7.25, d, 1H; 7.10, dt, 1H; 4.14, t, 2H; 2.26, t, 2H; 1.80-1.41, m, 6H.

1e: Preparation of Compound 5

A 3-neck 300 mL round-bottomed flask equipped with a reflux condenser, magnetic stir bar and an $N_2$ inlet was charged with 10 g (1 equivalent) of 2-hydroxybenzonitrile, absolute ethanol 400 mL, and 31.3 mL (1 equivalent) of sodium ethoxide. This mixture was stirred at 25° C. for 15 minutes. Ethyl 8-bromooctanoate (21 g, 1 equivalent) was then added dropwise over 15 minutes. The resulting mixture was heated to reflux (80° C.) for 72 hours.

The reaction mixture was cooled and the solids filtered off. The solvent was removed on a rotary evaporator. The crude residue was dissolved in methylene chloride (400 mL) and washed with saturated $NaHCO_3$ (3×100 mL), bleach (1×100 mL), $H_2O$ (1×50 mL) and brine (1×50 mL). The organic layer was dried to give the crude ester. The crude material was then dissolved in ethanol (200 mL) and water (20 mL). LiOH (8.6 g) was added and the resulting mixture was heated to reflux (80° C.) for 3 hours. The solution was cooled and the solvent removed. 150 mL of $H_2O$ was added and the aqueous solution was acidified to a pH of approximately 2 with concentrated HCl. The flask was cooled by placing it in a 4° C. refrigerator for 4 hours. A tan colored solid precipitated. This material was collected by vacuum filtration and dried on the high vacuum overnight to give 18 g of material (74% yield). This was further purified by recrystallization from ethyl acetate/hexanes (about 95/5) to give 15 g of 8-(2-cyanophenoxy) octanoic acid. Melting point: 83-85° C. Karl Fisher: 1.1%. Molecular Formula (with $H_2O$): $C_{15}H_{19}NO_3$*0.1613 $H_2O$. Combustion analysis (with $H_2O$ included): % C: 68.19 (calc'd), 68.53 (found); % H: 7.37 (calc'd), 7.33 (found); % N: 5.30 (calc'd), 5.34 (found). $^1$H NMR Analysis: ($d_6$-DMSO): δ 12.0, s, 1H (COOH); δ 7.71-7.60, m, 2H (aromatic CH's ortho and para to CN); δ 7.23, d, 1H, J=8.4 Hz (aromatic CH para to OR); δ 7.10, dt, 1H, J=0.7 and 6.7 Hz (aromatic CH ortho to OR); δ 4.13, t, 2H, J=6.4 Hz ($CH_2$ α to O); δ 2.22, t, 2H, J=7.3 Hz ($CH_2$ α to COOH); δ 1.73, m, 2H, ($CH_2$ α to O); δ 1.52-1.28, m, 8H (remaining aliphatic $CH_2$'s).

1f: Preparation of Compound 6

A 3-neck 300 mL round-bottomed flask equipped with a reflux condenser, magnetic stir bar and a nitrogen inlet was charged with 4 g (1 equivalent) of 2-hydroxybenzonitrile, absolute ethanol 140 mL, and 12.54 mL (1 equivalent) of sodium ethoxide. This mixture was stirred at 25° C. for 15 minutes. Ethyl 10-bromodecanoate (9.4 g, 1 equiv.) was then added dropwise over 10 minutes. The resulting mixture was heated to reflux (75° C.) for 72 hours.

The reaction mixture was cooled and the solids filtered off. The solvent was removed on a rotary evaporator. The crude residue was dissolved in ethyl acetate (300 mL) and washed with ½ saturated $NaHCO_3$ (2×100 mL), $H_2O$ (1×100 mL) and brine (1×50 mL). The organic layer was dried to give 10 g of the crude ester. The crude material was then dissolved in ethanol (100 mL) and water (20 mL). LiOH (3.3 g) was added and the resulting mixture was heated to reflux (75° C.) for 3 hours. The solution was cooled and the solvent removed. 20 mL of $H_2O$ was added and the aqueous solution was acidified to a pH of about 3 with concentrated HCl. The solution was transferred to a 4° C. refrigerator to cool. A tan colored solid began to precipitate. This material was collected by vacuum filtration and dried on the high vacuum overnight to give the crude acid. These solids were further purified by recrystallization from ethyl acetate/hexanes (95/5) to give 7.1 g of the product, 10-(2-cyanophenoxy)decanoic acid (78% yield). Melting point: 82-84° C. Molecular Formula with water: $C_{17}H_{23}NO_3$*0.0532. Combustion analysis: % C. 70.33 (calc'd), 69.82 (found); % H: 8.02(calc'd), 7.89(found); % N: 4.82 (calc'd), 4.82 (found).

1g: Preparation of Compound 7

A 3-neck 300 mL round-bottomed flask equipped with a reflux condenser, magnetic stir bar and an $N_2$ inlet was charged with 5 g (1 equivalent) of 2-hydroxy-5-chlorobenzonitrile, absolute ethanol 125 mL, and 12.16 mL (1 equivalent) of sodium ethoxide. This mixture was stirred at 25° C. for 15 minutes. Ethyl 5-bromovalerate (5.2 mL, 1 equivalent) was then added dropwise over 10 minutes. The resulting mixture was heated to reflux (75° C.) for 72 hours.

The reaction mixture was cooled and the solids filtered off. The solvent was removed on a rotary evaporator. The crude residue was dissolved in methylene chloride (200 mL) and washed with saturated $NaHCO_3$ (2×75 mL), $H_2O$ (1×100 mL) and brine (1×100 mL). The crude material was then dissolved in ethanol (120 mL) and water (10 mL). LiOH (4 g) was added and the resulting mixture was heated to reflux (75° C.) for 1 hours then stirred at ambient temperature overnight. The solvent was evaporated and 75 mL of $H_2O$ was added. The aqueous solution was acidified to a pH of about 3 with concentrated HCl and the flask cooled to 4° C. Tan colored solids precipitated. This material was collected by vacuum filtration and dried on the high vacuum overnight to give the crude acid. These solids were further purified by recrystallization from ethyl acetate/hexanes (95/5) (three times) to give 2.88 g of the product, 5-(4-chloro-2-cyanophenoxy)pentanoic acid (35% yield). Melting point: 87-90° C. Molecular Formula: $C_{12}H_{12}ClNO_3$. Combustion analysis: % C: 56.82(calc'd), 57.03(found); % H: 4.77(calc'd), 4.71(found); % N: 5.52 (calc'd), 5.45(found); Cl 13.98(calc'd), 13.93(found).

1h: Preparation of Compound 8

A 3-neck 300 mL round-bottomed flask equipped with a reflux condenser, magnetic stir bar and a nitrogen inlet was charged with 5 g (1 equivalent) of 4-hydroxybenzonitrile, absolute ethanol 150 mL, and 15.7 mL (1 equivalent) of sodium ethoxide. This mixture was stirred at 25° C. for 15 minutes. Ethyl 8-bromooctanoate (10.5 g, 1 equivalent) was then added dropwise over 10 minutes. The resulting mixture was heated to reflux (75° C.) for 72 hours.

The reaction mixture was cooled and the solids filtered off. The solvent was removed on a rotary evaporator. The crude residue was dissolved in methylene chloride (200 mL) and washed with saturated $NaHCO_3$ (2×75 mL), $H_2O$ (1×100 mL) and brine (1×100 mL). The crude material was then dissolved in ethanol (125 mL) and water (10 mL). LiOH (5 g) was added and the resulting mixture was heated to reflux (75° C.) for 1 hour then stirred at ambient temperature overnight. The solvent was evaporated and 75 mL of $H_2O$ was added. The aqueous solution was acidified to a pH of about 3 with concentrated HCl and the flask cooled to 4° C. An off-white colored solid precipitated. This material was collected by vacuum filtration and dried on the high vacuum overnight to give the crude acid. These solids were further purified by recrystallization from Ethyl acetate/hexanes (95/5) and again with chloroform to give 4.5 g of the product, 8-(4-cyanophenoxy)octanoic acid (41% yield). Melting point: 137-140° C. Molecular Formula: $C_{15}H_{19}NO_3$. Combustion analysis: % C: 68.94 (calc'd), 68.57 (found); % H: 7.33(calc'd), 7.13 (found); % N: 5.36 (calc'd), 5.28 (found).

1i: Preparation of Compound 9

Potassium hydroxide (15.02 g, 268.4 mmol) was ground in a mortar until powdered, then added to a 125 mL Erlenmeyer flask containing 50 mL of dimethylsulfoxide (DMSO), 8 g (6.71 mmol) of 2-hydroxybenzonitrile and 12.59 g (7.38 mmol) of 4-(chloromethyl)benzoic acid. The reaction was stirred at room temperature for six days. Distilled water (200 mL) was added to the brown reaction mixture, and the resulting solution was cooled to 4° C. Once cooled, the solution was acidified with concentrated HCl. The resulting solid was collected by vacuum filtration through a Buchner funnel. This material was purified by repeated recrystallizations from ethyl acetate to give 5.71 g of the product, 4-(2-cyanophenoxymethyl)benzoic acid. Melting point: 199-203° C. Combustion analysis: % C: 71.14 (calc'd), 70.89 (found); % H: 4.38 (calc'd), 4.35 (found); % N: 5.53 (calc'd), 5.25 (found); 1H NMR Analysis: (d6-DMSO): δ 8.0, d, 2H; δ 7.8, d, 1H; δ 7.75, t, 1H; δ 7.65, d, 2H; δ 7.4, d, 1H; δ 7.2, t, 1H; δ 5.44, s, 2H.

EXAMPLE 2

EXAMPLE 2A

Oral and Intacolonic Delivery of Heparin

Oral gavage (PO) and intracolonic (IC) dosing solutions containing a delivery agent compound and heparin sodium USP in 25% aqueous propylene glycol were prepared. Either the sodium salt of the delivery agent compound was used or the free acid was converted to the sodium salt with one equivalent of sodium hydroxide. Typically, the delivery agent compound and heparin (about 166-182 IU/mg) were mixed by vortex as dry powders. This dry mixture was dissolved in 25% v/v aqueous propylene glycol, vortexed and placed in a sonicator (about 37° C.). The pH was adjusted to about 7 (6.5 to 8.5) with aqueous NaOH (2N). The dosing solution was sonicated to produce a clear solution. The final volume was adjusted to 3.0 mL. The final delivery agent compound dose, heparin dose and volume dose amounts are listed below in Table 2.

The typical dosing and sampling protocols were as follows. Male Sprague-Dawley rats weighing between 275-350 g were fasted for 24 hours and were anesthetized with ketamine hydrochloride (88 mg/kg) intramuscularly immediately prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm 8 fr Rusch catheter was adapted to a 1 ml syringe with a pipette tip. The dosing catheter was inserted into the colon through the anus until the tube was no longer visible. The dosing solution was expressed slowly into the colon.

Citrated blood samples were collected by cardiac puncture following the administration of ketamine (88 mg/kg), typically at time—0.25, 0.5, 1.0 and 1.5 hours. Heparin activity was determined by utilizing the activated partial thromboplastin time (APTT) according to the method of Henry, J. B., Clinical Diagnosis and Management by Laboratory Methods, Philadelphia, Pa., W. B. Saunders (1979). Previous studied indicated baseline values of about 20 sec. Results from the five rats in each group were averaged for each time point. The maximum is reported below in Table 2.

TABLE 2

Oral and Intracolonic Delivery of Heparin

| Compound | Method of Administration | Volume Dose (ml/kg) | Compound Dose (mg/kg) | Heparin Dose (mg/kg) | Mean Peak APTT (sec) ± SD) |
|---|---|---|---|---|---|
| 3 | IC | 200 | 25 | 1 | 16.23 ± 1.23 |
| 3 | Oral | 300 | 100 | 1 | 203.59 ± 72.97 |
| 5 | IC | 50 | 25 | 1 | 80.22 ± 45.70 |
| 5 | Oral | 300 | 100 | 1 | 176.25 ± 175.01 |

EXAMPLE 2B

Oral Delivery of Recombinant Human Growth Hormone (rhGH)

Oral gavage (PO) dosing solutions of delivery agent compound and rhGH in phosphate buffer were prepared. A solution of the delivery agent compound was made either with the sodium salt of the compound or by converting the free acid to its sodium salt. Typically, a solution of the delivery agent compound was prepared in phosphate buffer and stirred, adding one equivalent of sodium hydroxide (1.0 N) when making sodium salt. The final dosing solutions were prepared by mixing the delivery agent compound with an rhGH stock solution (15 mg rhGH/ml) and diluting to the desired volume (usually 3.0 ml). The delivery agent compounds and rhGH dose amounts are listed below in Table 3.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger.

Blood samples were collected serially from the tail artery, typically at time=0, 15, 30, 45, 60 and 90 minutes for oral dosing. The five samples from each time period were pooled. Serum rHGH concentrations were quantified by an rHGH immunoassay test kit (Kit #K1F4015 from Genzyme Corporation Inc., Cambridge, Mass.). Previous studies indicated baseline values of about zero.

The maximum concentration for each group is reported below in Table 3.

TABLE 3

Oral Delivery of rhGH in Rats

| Compound | Compound Dose (mg/kg) | rhGH Dose (mg/kg) | Volume Dose (ml/kg) | Peak Serum [rhGH] (ng/ml) ± SD (SE) |
|---|---|---|---|---|
| 1 | 200 | 3 | 1 | 0 |
| 3 | 200 | 3 | 1 | 57.51 ± 60.97 (26.97) |
| 4 | 200 | 3 | 1 | 11.52 ± 12.23 |
| 4 | 200 | 3 | 1 | 73.13 ± 73.69 |
| 9 | 200 | 3 | 1 | 57.53 ± 45.27 (20.24) |

EXAMPLE 2C

Oral Delivery of Cromolyn

Dosing solutions containing a delivery agent compound and cromolyn, disodium salt (cromolyn) (from Sigma Chemicals of St. Louis, Mo.) were prepared in deionized water. The free acid of the delivery agent compound was converted to the sodium salt with one equivalent of sodium hydroxide. This mixture was vortexed and placed in a sonicator (about 37° C.). The pH was adjusted to about 7-7.5 with aqueous NaOH. Additional NaOH was added, if necessary, to achieve uniform solubility, and the pH re-adjusted. The mixture was vortexed to produce a uniform solution, also using sonication and heat if necessary. The delivery agent compound solution was mixed with cromolyn from a stock solution (175 mg cromolyn/ml in deionized water, pH adjusted, if necessary, with NaOH or HCl to about 7.0, stock solution stored frozen wrapped in foil, then thawed and heated to about 30° C. before using). The mixture was vortexed to produce a uniform solution, also using sonication and heat if necessary. The pH was adjusted to about 7-7.5 with aqueous NaOH. The solution was then diluted with water to the desired volume (usually 2.0 ml) and concentration and stored wrapped in foil before use. The final delivery agent compound and cromolyn doses, and the dose volumes are listed below in Table 4.

The typical dosing and sampling protocols were as follows. Male Sprague-Dawley rats weighing between 200-250 g were fasted for 24 hours and were anesthetized with ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected via the tail artery, typically at 0.25, 0.5, 1.0 and 1.5 hours after dosing. Serum cromolyn concentrations were measured by HPLC. Samples were prepared as follows: 100 µl serum was combined with 100 µl 3N HCl and 300 µl ethyl acetate in an eppendorf tube. The tube was vortexed for 10 minutes and then centrifuged for 10 minutes at 10,000 rpm. 200 µl ethyl acetate layer was transferred to an eppendorf tube containing 67 µl 0.1 M phosphate buffer. The tube was vortexed for 10 minutes and then centrifuged for 10 minutes at 10,000 rpm. The phosphate buffer layer was then transferred to an HPLC vial and injected into the HPLC (column=Keystone Exsil Amino 150×2 mm i.d., 5 µm, 100 Å; mobile phase=35% buffer(68 mM $KH_2PO_4$ adjusted to pH 3.0 with 85% $H_3PO_4$)/65% acetonitrile; injection volume=10 µl; flow rate=0.30 ml/minute; cromolyn retention time=5.5 minutes; absorbance detected at 240 nm). Previous studies indicated baseline values of about zero.

Results from the animals in each group were averaged for each time point and the highest of these averages (i.e., mean peak serum cromolyn concentration) is reported below in Table 4.

TABLE 4

Cromolyn - Oral Delivery

| Compound | Compound Dose (mg/kg) | Cromolyn Dose (mg/kg) | Volume Dose (ml/kg) | Mean Peak serum [cromolyn] (µg/ml) ± SD (SE) |
|---|---|---|---|---|
| 3 | 200 | 25 | 1 | 0.62 ± 0.29 (0.13) |
| 4 | 200 | 25 | 1 | 0.82 ± 0.65 (0.29) |
| 5 | 200 | 25 | 1 | 0.46 ± 0.22 (0.10) |
| 9 | 200 | 25 | 1 | 0.40 ± 0.21 (0.10) |

Insulin—Oral Delivery

Oral dosing (PO) compositions of delivery agent compound and human zinc insulin (minimum 26 IU/mg available from Calbiochem—Novabiochem Corp, La Jolla, Calif.) were prepared in deionized water. Typically, 500 mg of delivery agent compound was added to 1.5 ml of water. The free acid of the delivery agent compound was converted to the sodium salt by stirring the resultant solution and adding one equivalent of sodium hydroxide. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted to about 7 to 8.5. Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 10N NaOH and 50 ml 1N NaOH) was added to the solution and mixed by inverting. The solution may be used in the dosing protocol immediately, or alternatively, the solution may be placed into a 37° C. water bath for one hour prior to dosing. The final delivery agent compound dose, insulin dose and dose volume amounts are listed below in Table 5.

The typical dosing and sampling protocols were as follows. Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=15, 30, 60, 120 and 180 minutes. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum human insulin concentrations (µU/ml) were measured for each time point for each of the five animals in each dosing group. The five values for each time point were averaged and the results plotted as serum insulin concentration versus time. (Previous experiments revealed no measurable levels of human insulin following oral dosing with human insulin alone.) The maximum (peak) and the area under the curve (AUC) are reported below in Table 5.

TABLE 5

Insulin - Oral Delivery

| Delivery Agent Compound # | Delivery Agent Compound Dose (mg/kg) | Insulin Dose (mg/kg) | Volume Dose (ml/kg) | Mean Peak Serum Human Insulin |
|---|---|---|---|---|
| 1 | 200 | 0.5 | 1.0 | 218.74 ± 361.02 (IU/ml ± SD) |
| 2 | 200 | 0.5 | 1.0 | 595.45 ± 1123.42 (IU/ml ± SD) |
| 2 | 200 | 0.5 | 1.0 | 22.88 ± 34.87 (µU/ml ± SD) |
| 3 | 200 | 0.5 | 1.0 | 1.57 ± 3.44 (µU/ml ± SD) |
| 3 | 200 | 0.5 | 1.0 | 338.67 ± 456.61 (µU/ml ± SD) |
| 3 | 200 | 0.5 | 1.0 | 0.23 ± .60 (µU/ml ± SD) |
| 3 | 200 | 0.5 | 1.0 | 267.53 ± 586.97 (µU/ml ± SD) |
| 3 | 200 | 0.5 | 1.0 | 0.48 ± 1.18 (µU/ml ± SD) |
| 3 | 200 | 0.5 | 1.0 | 89.53 ± 60.14 (µU/ml ± SD) |
| 3 | 200 | 0.5 | 1.0 | 5.70 ± 4.04 (µU/ml ± SD) |
| 3 | 200 | 0.5 | 1.0 | 18.24 ± 21.24 (µU/ml ± SD) |
| 3 | 200 | 0.5 | 1.0 | 5.81 ± 6.96 (µU/ml ± SD) |
| 3 | 200 | 0.5 | 1.0 | 222.74 ± 135.16 (µU/ml ± SD) |
| 3 | 200 | 0.5 | 1.0 | 101.75 ± 79.39 (µU/ml ± SD) |
| 4 | 200 | 0.5 | 1.0 | 559 ± 410 (µU/ml ± SD) |
| 5 | 100 | 3 | 0.5 | 695.13 ± 921.15 (µU/ml ± SD) |
| 5 | 200 | 0.5 | 0.5 | 669.40 ± 847.88 (µU/ml ± SD) |
| 5 | 200 | 0.5 | 1.0 | 109.37 ± 119.44 (µU/ml ± SD) |
| 5 | 200 | 0.5 | 1.0 | 185.76 ± 94.24 (µU/ml ± SD) |
| 5 | 200 | 0.5 | 1.0 | 153.19 ± 114.61 (µU/ml ± SD) |
| 5 | 200 | 0.5 | 1.0 | 323.76 ± 177.89 (µU/ml ± SD) |
| 5 | 200 | 0.5 | 1.0 | 53.44 ± 39.90 (µU/ml ± SD) |
| 5 | 200 | 0.5 | 1.0 | 99.83 ± 76.37 (µU/ml ± SD) |
| 6 | 200 | 0.5 | 1.0 | 0.33 ± 0.69 (µU/ml ± SD) |
| 6 | 200 | 0.5 | 1.0 | 1.99 ± 3.29 (µU/ml ± SD) |
| 7 | 200 | 0.5 | 1.0 | 62.15 ± 56.42 (µU/ml ± SD) |
| 7 | 200 | 0.5 | 1.0 | 91.22 ± 44.59 (µU/ml ± SD) |
| 8 | 200 | 0.5 | 1.0 | 8.18 ± 5.01 (µU/ml ± SD) |
| 9 | 200 | 0.5 | 1.0 | 443.31 ± 632.53 (µU/ml ± SD) |

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A method of regulating reproductive function in a patient in need thereof comprising administering an effective amount of a composition comprising:
   (A) an active agent; and
   (B) at least one compound having the formula:

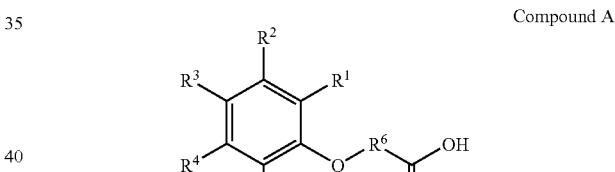

Compound A or a salt thereof, wherein
$R^1$, $R^2$, $R^3$, $R^4$ and $R^5$ are independently H, —CN, —OH, —OCH$_3$, or halogen, at least one of $R^1$, $R^2$, $R^3$, $R^4$ and $R^5$ being —CN; and
$R^6$ is $C_1$-$C_{12}$ linear or branched alkylene, alkenylene, arylene, alkyl(arylene) or aryl(alkylene),
with the proviso that when $R^1$ is —CN, $R^4$ is H or —CN, and $R^2$, $R^3$, and $R^2$ are H, then $R^6$ is not $(CH_2)_1$.

2. The method of claim 1, wherein the active agent is luteinzing hormone releasing hormone.

3. A method of regulating reproductive function in a patient in need thereof comprising administering an effective amount of a composition comprising:
   (A) an active agent; and
   (B) a compound selected from the group consisting of:

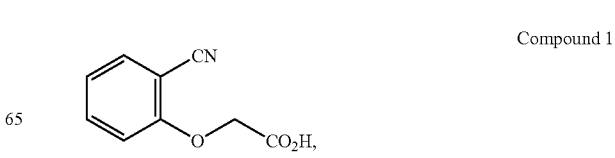

Compound 1

-continued

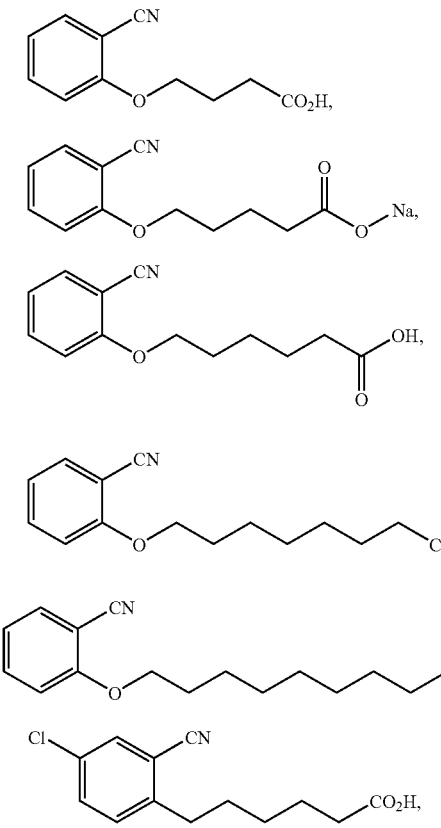

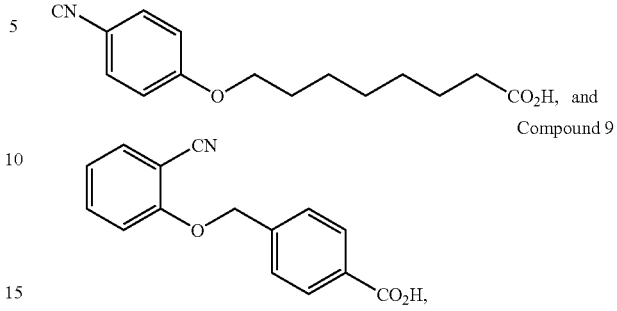

and salts thereof.

4. The method of claim 3 wherein the active agent is luteinizing hormone releasing hormone.

5. The method of claim 1 wherein the active agent is follicle stimulating hormone.

6. The method of claim 3 wherein the active agent is follicle stimulating hormone.

7. The method of claim 3, wherein the delivery agent is selected from compounds 1, 3, 4 and 9 and salts thereof.

8. The method of claim 4, wherein the delivery agent is selected from compounds 1, 3, 4and 9and salts thereof.

9. The method of claim 6, wherein the delivery agent is selected from compounds 1, 3, 4and 9and salts thereof.

* * * * *